United States Patent [19]

Illuminati et al.

[11] 4,182,726
[45] Jan. 8, 1980

[54] PROCESS FOR THE PREPARATION OF AROMATIC CARBONATES

[75] Inventors: Gabriello Illuminati, Rome; Ugo Romano, Milan; Renato Tesei, San Donato Milanese, all of Italy

[73] Assignee: Snamprogetti, S.p.A., San Donato Milanese, Italy

[21] Appl. No.: 782,164

[22] Filed: Mar. 28, 1977

Related U.S. Application Data

[63] Continuation of Ser. No. 586,353, Jun. 12, 1975, abandoned.

[30] Foreign Application Priority Data

Jun. 25, 1974 [IT] Italy .................. 24392 A/74
Feb. 12, 1975 [IT] Italy .................. 20191 A/75
Apr. 18, 1975 [IT] Italy .................. 22472 A/75

[51] Int. Cl.² ........................... C07C 68/06
[52] U.S. Cl. .................... 260/463; 260/453 RW; 260/455 B
[58] Field of Search ................... 260/463, 47 XA

[56] References Cited

U.S. PATENT DOCUMENTS

| 2,789,964 | 4/1957 | Reynolds et al. | 260/47 XA |
| 3,655,626 | 4/1972 | Kolobielski | 260/463 |
| 3,721,693 | 3/1973 | Fein | 260/463 |
| 4,045,464 | 8/1977 | Romano et al. | 260/463 |

OTHER PUBLICATIONS

Knoerr et al., Chemical Abstracts, 59:9809d.

*Primary Examiner*—Lewis Gotts
*Assistant Examiner*—Molly C. Eakin
*Attorney, Agent, or Firm*—Morgan, Finnegan, Pine, Foley & Lee

[57] ABSTRACT

An aromatic carbonate having the formula:

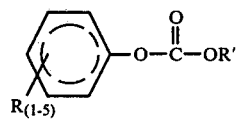

or

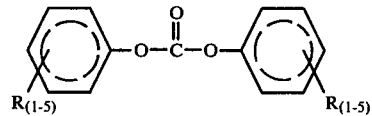

wherein R' is alkyl and R is alkyl, alkoxy, aryl, aryloxy or $NO_2$, is prepared by reacting the related phenol or an acyl ester thereof with an alkyl, cyclic or aryl-alkyl carbonate in the presence of a catalyst such as $AlCl_3$.

4 Claims, No Drawings

PROCESS FOR THE PREPARATION OF AROMATIC CARBONATES

This is a continuation of application Ser. No. 586,353, filed June 12, 1975, now abandoned.

The present invention relates to a process for the preparation of aromatic carbonates having the formula

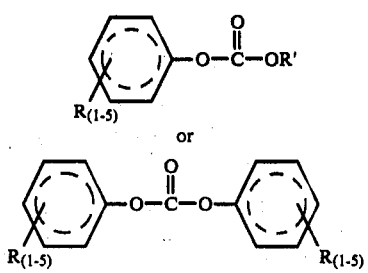

in which R' is an alkyl group and R is a substituent selected from alkyl, alkoxy, aryl, aryloxy and $NO_2$ groups.

It is known that such compounds are prepared starting from the respective phenols through a reaction with phosgene or chloroformates according to complex technologies, which provide several risks due to the toxicity of the employed reagents and give rise to the formation, as by-product, of hydrochloric acid.

On the other hand it is also known that it is possible to react phenols and alkyl carbonates in the presence of strong bases as catalyst. Such a reaction has however the drawback of low reaction rates and the formation of high amounts of phenol ether as by-products.

The aromatic carbonates are of remarkable industrial interest since they are employed as intermediates in the production of aromatic polycarbonates and in the synthesis of some isocyanates.

It has now been found, which is the subject of the present invention, that it is possible to obtain, at high yields and selectivities, aryl-alkyl carbonates and diaryl carbonates by reacting the respective phenol or acyl ester thereof with an alkyl, cyclic or aryl-alkyl carbonate, in the presence of a suitable catalyst.

The reaction is carried out in the liquid phase, with or without solvent, at temperatures of from 25° to 350° C., preferably from 80° to 250° C., and pressures of from 0.1 to 100 atmospheres, preferably from 1 to 25 atmospheres.

The molar ratio between phenol compound and carbonate may range from 100:1 to 1:100, preferably from 5:1 to 1:10. Efficient catalysts are compounds having the formulae $AlX_3$, $TiX_3$, $UX_4$, $TiX_4$, $VOX_3$, $VX_5$, $ZnX_2$, $FeX_3$, $SnX_4$, wherein X is halogen, acetoxy, alkoxy, aryloxy or a Lewis acid, under the general definition thereof, or the transition metal or metal compounds generating the same.

The Lewis acids may be employed as such or mixed with one another; or use may be made of adducts thereof with organic molecules.

The inventive process may be utilized for preparing aromatic derivatives other than the aforesaid ones, for instance aromatic thiocarbonates or imidocarbonates starting from the corresponding alkyl compounds.

Moreover it is possible (as a further aspect of the present invention) to prepare polymer aromatic carbonates containing in the molecule repeated units of the type —(A—O—CO—O)— in which A is a divalent radical containing at least one aromatic function, such a preparation being carried out simply by letting the aforesaid reaction be followed by the removal of alkyl carbonate.

In order to illustrate the employed apparatus we describe, hereinafter, a possible type thereof, which, however, must not be thought to be limitative of the inventive object.

The reagents and the catalyst were charged in a 2 l volume flask supporting a 10 plate column provided with a liquid-dividing head: low boiling alcohol was continuously distilled as such or in the form of azeotrope. The reaction is preferably carried out under an inert gas atmosphere, reagents and solvent having been suitably made free from water.

EXAMPLE 1

The reaction between dimethylcarbonate (DMC) and phenol (phen) was carried out in the presence of anhydrous $AlCl_3$ in the molar ratio DMC/phen/cat=5/1/0.05. The temperature was 98° C., the methyl alcohol -DMC azeotrope was distilled at a reflux ratio of 10:1. After 8 hours obtained a phenol conversion equal 15.5% at a Ph MC selectivity of 95% (Ph MC=phenylmethylcarbonate), the remaining 5% of phenol being converted to anisole.

EXAMPLE 2

The reaction was carried out under the same conditions as Example 1 but the catalyst that was $TiCl_3$. After 5.5 hours we obtained a 13% conversion with respect to phenol at a Ph MC selectivity higher than 99%.

EXAMPLE 3

The reaction was carried out as in Example 1. $TiCl_4$ was the catalyst. After 8 hours we obtained a 23% conversion and a total selectivity to Ph MC.

EXAMPLE 4

Under the same conditions as Example 1, Ti(O-isopropyl)$_4$ was employed as catalyst. After 8 hours we obtained 11% conversion and a practically total selectivity to Ph MC.

EXAMPLE 5

Under the same conditions as Example 1, Ti(Oφ)$_4$ was employed as catalyst. After 24 hours we obtained a 41.5% conversion and a selectivity to Ph MC of 95%, the remaining part being diphenylcarbonate (DPhC). Anisole was present only in trace amounts, that could not be evaluated from an analytical point of view.

EXAMPLE 6

Under the same conditions as Example 1, $VCl_4$ was the catalyst. A 3% conversion and a total selectivity to phenylmethylcarbonate were obtained.

EXAMPLE 7

$VOCl_3$ was employed as catalyst under the operating conditions of Example 1. After 5 hours we obtained a 5% phenol conversion and a total selectivity to phenylmethylcarbonate.

EXAMPLE 8

Under the same conditions as Example 6, the operations were carried out at a DMC/phen/Ti(Oφ)$_4$ ratio of 10/1/0.05. After 8 hours, the phenol conversion was 21% and the selectivity to PhMC was practically total.

EXAMPLE 9

The reaction was carried out on a mixture formed by DMC/phen/TiCl=1/4/0.05 in the presence of n-hexane in an amount corresponding to 35 g per mole of DMC. A mixture consisting of hexane/DMC/Methyl alcohol was distilled at a reflux ratio of 10/1 and there was continuously added a hexane/DMC mixture so as to reinstate the portion removed by distillation. The reaction temperature was 135° C. After 8 hours the phenol conversion was 9% at a ph MC selectivity of 78% and a DPhC selectivity of 22%.

EXAMPLE 10

The reaction was carried out at 130° C. on a mixture constituted by p-cresol/DEC (diethylcarbonate)/Ti(O-iC$_3$H$_7$)$_4$=1/5/0.05 for 3 hours. A 25% conversion and a total selectivity to tolyl-ethyl-carbonate were obtained.

EXAMPLE 11

A mixture of DEC/hydroquinone-monomethylether/Ti (O-i C$_3$H$_7$)$_4$ in the ratio 5/1/0.05 was reacted at 130° C. for three hours. A 36% conversion and a practically total selectivity to p-methoxyphenylcarbonate were obtained.

EXAMPLE 12

Phenylethylcarbonate was reacted with phenol in the presence of Ti(O$\phi$)$_4$ in the molar ratio 1/0.8/0.04 at 180° C., in the presence of heptane. There was continuously distilled a mixture constituted by n-heptane-ethyl alcohol and n-heptane was added to replace what was distilled.

After 4 hours a 42% conversion of phenol and a total selectivity to diphenylcarbonate were obtained.

EXAMPLE 13

Use was made of a stainless steel reactor having 2.4 l volume on which was put a steel distillation column having 1" diameter and 1 m length with glass Raschig rings.

The reaction was carried out at 180° C. at 6.6 atmospheres by continuously distilling the methyl alcohol, DMC azeotrope and renewing DMC removed through the distillation. The DMC/phen/Ti(O$\phi$)$_4$ molar ratio was 5/1/0.5. After 7 hours reaction, there were obtained a 53% phenol conversion and 95% selectivity to PhMC and 5% to DPhC.

EXAMPLE 14

Under the same conditions as Example 1, SnCl$_4$ was employed as catalyst. The conversion was 8%, the selectivity to phenylmethylcarbonate was 85% and to phenylmethylether was 15%.

EXAMPLE 15

A mixture of DEC/phen/UCl$_4$ was reacted, in a 5/1/0.075 ratio, at 130° C. for 4 hours. A phenol conversion of 38% was obtained as selectivities of 98% as to PhEC and 2% as to DEC.

EXAMPLE 16

A mixture of DEC/p-nitrophenol/Ti(O$\phi$)$_4$ in the ratio 5/1/0.05 was reacted at 130° C. for 4 hours.

A p-nitrophenol conversion of 10% and a total selectivity to p-nitrophenylcarbonate were obtained.

EXAMPLE 17

Use was made of a 250 cc flask supporting a distillation column with 20 plates and a liquid-dividing head; therein, at 145° C., were charged 68 g of phenyl acetate, 60 g of diethylcarbonate and 2 g of titanium phenate. By continuously head distilling ethyl acetate, after 4 hours reacting, there were obtained 68% by mole of diphenyl carbonate and 30% by mole of phenyl-ethyl carbonate at a total selectivity higher than 98% and a 95% conversion of phenyl acetate.

EXAMPLE 18

In the aforesaid apparatus, at 145° C., were charged 74 g of phenyl acetate and, gradually, 90 g of dimethyl carbonate and 1 g of titanium tetramethoxide. Methyl acetate being continuously distilled, after 4 hours there were obtained 80% by mole of diphenyl carbonate and 18% by mole of phenyl methyl carbonate, at selectivity higher than 98% and 97% conversion of methyl acetate.

EXAMPLE 19

In the same apparatus described in Example 17 were charged, at 150° C., 68 g of phenyl acetate, 80 g of phenyl methyl carbonate and 25 cc of n-heptane with 1.5 g of aluminum ethylate.

Methyl acetate was continuously distilled and, after 4 hours, there was obtained a 90% conversion of the reactants at a 98% selectivity to diphenyl carbonate.

EXAMPLE 20

At 140°–150° C., 150 g of bisphenol A bis acetate and 3 cc of titanium tetraisopropylate were added to the aforesaid apparatus, then 130 cc of diethylcarbonate were gradually added while ethyl acetate was continuously distilled from the system.

After 10 hours there was obtained a total conversion of bisphenol acetate to bisphenol A—bis ethyl carbonate.

EXAMPLE 21

In the same aforesaid apparatus there were charged 150 g of bisphenol A bisacetate and 3 g of aluminum tetraisopropylate, at 150°–170° C., and there were gradually added 110 cc of dimethyl carbonate, methyl acetate being continuously distilled.

After 8 hours a complete conversion was obtained to bisphenol bis methyl carbonate.

EXAMPLE 22

190 g of bisphenol A bis-acetate and 2.5 g of Ti(O-iso C$_3$H$_7$)$_4$ were charged into a 250 cc flask supporting a 30 plates distillation column equipped with liquid-dividing head. The mixture was heated to 150°–170° C. and then gradually there was added 160 cc of dimethylcarbonate. At the same time formed methyl acetate was distilled away. At the reaction end the system was brought under vacuum and the temperature raised to 270° C.

Dimethylcarbonate, distilled during the reaction, was recovered by a cold trap. After 4 hours there was obtained a polymer having an average molecular weight equal to 17,000 and a structure equal to that of the commercial aromatic polycarbonates.

EXAMPLES 23–24

Two tests were carried out according to the procedure of the foregoing example. The amounts of the employed compounds and the obtained results are reported in the following table.

| Alkyl carbonate | Catalyst | Bisphenol acetate | Polymer Molecular Weight |
| --- | --- | --- | --- |
| Diethylcarbonate 150 cm³ | Ti(Oφ)₄ 2.5 g | 150 g | 14,000 |
| dimethylcarbonate 150 cm³ | Al (φ-sec butyl)₃ 3 g | 150 g | 5,600 |

What we claim is:

1. The process of preparing an aromatic carbonate having the formula:

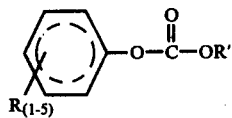

or

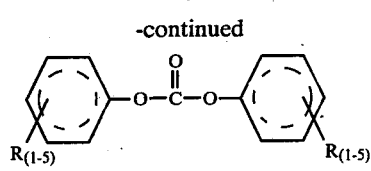

wherein R' is alkyl and R is a member of the group consisting of H, alkyl, alkoxy, aryl, aryloxy and $NO_2$, which comprises reacting a phenolic compound consisting of the respective phenol, or an acyl ester thereof, with an alkyl or aryl-alkyl carbonate in the presence of a catalyst selected from the group consisting of $AlX_3$, $UX_3$, $TiX_3$, $TiX_4$, $VOX_3$, $VX_5$, $ZnX_2$, $FeX_3$ and $SnX_4$, wherein X is a member of the group consisting of halogen, alkoxy, aryloxy and acetoxy, in the liquid phase, at a temperature in the range of from 25° to 350° C., at a pressure in the range of from 0.1 to 100 atmospheres, and wherein the phenol/carbonate ratio is from 100:1 to 1:100.

2. The process as claimed in claim 1, wherein said phenolic compound is a member of the group consisting of phenol, p-cresol, hydroquinone-monoethyl ether, p-nitrophenol, phenylacetate and bisphenol A bisacetate.

3. The process as claimed in claim 1, wherein said alkyl or aryl-alkyl carbonate is a member of the group consisting of dimethylcarbonate, diethylcarbonate, phenylethylcarbonate and phenylmethylcarbonate.

4. The process as claimed in claim 3, wherein said phenolic compound is a member of the group consisting of phenol, p-cresol, hydroquinone-monoethyl ether, p-nitrophenol, phenylacetate and bisphenol A bisacetate.

* * * * *